United States Patent
Bouchiat et al.

(10) Patent No.: US 9,105,793 B2
(45) Date of Patent: Aug. 11, 2015

(54) GRAPHENE DEVICE AND METHOD OF USING GRAPHENE DEVICE

(75) Inventors: Vincent Bouchiat, Kensington, CA (US); Caglar Girit, Saint Cloud (FR); Brian Kessler, Oakland, CA (US); Alexander K. Zettl, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 756 days.

(21) Appl. No.: 12/916,353

(22) Filed: Oct. 29, 2010

(65) Prior Publication Data

US 2011/0102068 A1 May 5, 2011

Related U.S. Application Data

(60) Provisional application No. 61/256,932, filed on Oct. 30, 2009.

(51) Int. Cl.
| | |
|---|---|
| *H01L 29/12* | (2006.01) |
| *H01L 39/12* | (2006.01) |
| *G01N 27/414* | (2006.01) |
| *H01L 39/14* | (2006.01) |
| *H01L 29/16* | (2006.01) |

(52) U.S. Cl.
CPC .......... *H01L 39/121* (2013.01); *G01N 27/4146* (2013.01); *H01L 39/146* (2013.01); *H01L 29/1606* (2013.01)

(58) Field of Classification Search
CPC ............. G01N 27/414; G01N 27/4146; H01L 39/146; H01L 39/121; H01L 29/1606

USPC ................... 257/E39.006–E39.008, E51.039, 257/E39.001

See application file for complete search history.

(56) References Cited

U.S. PATENT DOCUMENTS

| | | | |
|---|---|---|---|
| 5,465,046 A * | 11/1995 | Campbell et al. ............. | 324/244 |
| 2005/0212014 A1 * | 9/2005 | Horibe et al. ................. | 257/213 |
| 2007/0187694 A1 * | 8/2007 | Pfeiffer .......................... | 257/76 |
| 2009/0174435 A1 * | 7/2009 | Stan et al. .................... | 326/112 |
| 2009/0236609 A1 * | 9/2009 | de Heer et al. ............... | 257/77 |

OTHER PUBLICATIONS

Ahn et al., "Electostatic modification of novel materials," Reviews of Modern Physics, vol. 78, No. 4, pp. 1185-1212, (2006).

(Continued)

*Primary Examiner* — Laura Menz
*Assistant Examiner* — Candice Y Chan
(74) *Attorney, Agent, or Firm* — Lawrence Berkeley National Laboratory

(57) ABSTRACT

An embodiment of a graphene device includes a layered structure, first and second electrodes, and a dopant island. The layered structure includes a conductive layer, an insulating layer, and a graphene layer. The electrodes are coupled to the graphene layer. The dopant island is coupled to an exposed surface of the graphene layer between the electrodes. An embodiment of a method of using a graphene device includes providing the graphene device. A voltage is applied to the conductive layer of the graphene device. Another embodiment of a method of using a graphene device includes providing the graphene device without the dopant island. A dopant island is placed on an exposed surface of the graphene layer between the electrodes. A voltage is applied to the conductive layer of the graphene device. A response of the dopant island to the voltage is observed.

28 Claims, 6 Drawing Sheets

(56) References Cited

OTHER PUBLICATIONS

Ahn et al., "Electric field effect in correlated oxide systems," Nature, vol. 424, pp. 1015-1018, (Aug. 28, 2003).

Hwang, "Atomic control of the electron structure at complex oxide heterointerfaces," MRS Bulletin, vol. 31, pp. 28-35, (Jan. 2006).

Takahashi et al., "Local switching of two-dimensional superconductivity using the ferroelectric field effect," Nature, vol. 441, pp. 195-198, (May 11, 2006).

Ueno et al., "Electric-field-induced superconductivity in an insulator," Nature Materials, vol. 7, pp. 855-858, (Nov. 2008).

Caviglia et al., "Electric field control of the LaAlO3/SrTiO3 interface ground state," Nature, vol. 456, pp. 624-627, (2008).

Siemons et al., "Origin of charge density at LaAlO3 on SrTiO3 heterointerfaces: Possibility of intrinsic doping," Physical Review Letters, vol. 98, No. 19, pp. 196802-1-1986802-4, (May 11, 2007).

Novoselov et al., "Two-dimensional atomic crystals", Proceedings of the National Academy of Sciences, vol. 102, No. 30, pp. 10451-10453, (Jul. 26, 2005).

Li et. al., "Large-area synthesis of high-quality and uniform graphene films on copper foils," Science, vol. 324, pp. 1312-1314, (Jun. 5, 2009).

Geim & Novoselov, "The rise of graphene", Nature Materials, vol. 6, pp. 183-191, (Mar. 2007).

Feigel'man et al., "Proximity-induced superconductivity in graphene," JETP Letters, vol. 88, No. 11, pp. 862-866, (2008).

Lutchyn et al., "Dissipation-driven quantum phase transition in superconductor-graphene systems," Physical Review Letters, vol. 101, pp. 106402-1-106402-4, (Sep. 5, 2008).

Giovannetti et al., "Doping graphene with metal contacts," Physical Review Letters, vol. 101, pp. 026803-1-026803-4, (Jul. 11, 2008).

Lee et al., "Contact and edge effects in graphene devices," Nature Nanotechnology, vol. 3, pp. 486-490, (Aug. 2008).

Chen et al., "Charged-impurity scattering in graphene," Nature Physics, vol. 4, pp. 377-381, (May 2008).

Grit et al., "Tunable Graphene dc Superconducting Quantum Interference Device," Nano Letters, vol. 9, No. 1, pp. 198-199, (2009).

Kosterlitz et al., "Ordering, metastability and phase transitions in two-dimensional systems," Journal of Physics C: Solid State Physics, vol. 6, pp. 1181-1203, (1973).

Heersche et al., "Bipolar supercurrent in graphene," Nature, vol. 446, pp. 56-59, (Mar. 1, 2007).

Du et al., "Josephson current and multiple Andreev reflections in graphene SNS junctions," Physical Review B, vol. 77, pp. 184507-1-184507-5 (2008).

Tombros et al., "Electronic spin transport and spin precession in single graphene layers at room tempurature," Nature, vol. 448, pp. 571-575, (Aug. 2, 2007).

Heyraud and Métois, "Equilibrium Shape and Temperature; lead on graphite," Surface Science, vol. 128, pp. 334-342, (1983).

Zayed and Elasayed-Ali, "Melting behavior of as-deposited and recrystallized indium nanocrystals," Thin Solid Films, vol. 489, pp. 42-49, (2005).

Farmer et al., Chemical Doping and Electron-Hole Conduction Asymmetry in Graphene Devices, Nano Letters, vol. 9, No. 1, pp. 388-392, (2009).

Huard et al., "Evidence of the role of contacts on the observed electron-hole assymetry in graphene," Physical Review B, vol. 78, pp. 121402-1-121402-4, (2008).

Aslamazov and Larkin, The Influence of fluctuation pairing of electrons on the conductivity of normal metal, Physics Letters, vol. 26A, No. 6, pp. 238-239, (Feb. 12, 1968).

Beasley and Mooij, Possibility of Vortex-Antivortex Pair Dissociation in Two-Dimensional Superconductors, Physical Review Letters, vol. 42, No. 17, pp. 1165-1168, (Apr. 23, 1979).

Epstein et al., "Renormalization effects near the vortex-unbinding transition of two-dimensional superconductors," Physical Review B, vol. 26, No. 7, pp. 3950-3953, (Oct. 1, 1982).

Teitel and Jayaprakash, "Josephson-Junction Arrays in Transverse Magnetic Fields," Physical Review Letters, vol. 51, No. 21, pp. 1999-2002, (Nov. 21, 1983).

Park et al., "Electron Beam Supercollimation in Graphene Superlattices," Nano Letters, vol. 8, No. 9, pp. 2920-2924, (2008).

\* cited by examiner

GRAPHENE DEVICE AND METHOD OF USING GRAPHENE DEVICE

RELATED APPLICATIONS

The application claims priority to U.S. Provisional Patent Application Ser. No. 61/256,932, filed Oct. 30, 2009, which is herein incorporated by reference in its entirety.

STATEMENT OF GOVERNMENT SUPPORT

This invention was made with government support under Contract No. DE-AC02-05CH11231 awarded by the U.S. Department of Energy. The government has certain rights in this invention.

BACKGROUND OF THE INVENTION

The present invention relates to the field of graphene and, more particularly, to the field of graphene devices.

Phase transitions are a dramatic example of macroscopic order arising from the microscopic interactions in a physical system. Small changes in the coupling strength of the microscopic interaction can produce distinctly different orderings. This coupling can depend on a variety of external factors such as temperature, magnetic field, or pressure. However, in any electronic phase transition, the coupling strength invariably depends on one essential factor, the density of electrons between interacting elements.
Need Using the electric field-effect to tune the conductivity of semiconductors forms the physical basis of the consumer electronics industry. However, the ability to tune other electronic properties such as superconductivity and ferromagnetism (see, Ahn, C. H. et al., *Rev. Mod. Phys.* 78, 1185-1212 (2006) and Ahn, C. H., et al., *Nature* 424, 1015-1018 (2003).) has met with relatively limited success despite significant applications. The major obstacle to this end has been finding materials which not only have the requisite electronic properties but that can also be gated.

PRIOR ART

Recent advances in the fabrication of exotic materials such as complex oxide interfaces (See, Hwang, H. Y., *MRS Bull.* 31, 28-35 (2006).) and novel dielectrics (See, Takahashi, K. S. et al., *Nature* 441, 195-198 (2006) and Ueno, K. et al., *Nat. Mater.* 7, 855-858 (2008).) have resulted in the control of low temperature superconducting states (See, Caviglia, A. D. et al., *Nature* 456, 624-627 (2008).) via the field effect, but the choice of electronic order is limited by material compatibility and disorder remains hard to control (See, Siemons, W. et al., *Phys. Rev. Lett.* 98, 4 (2007).).

Another tactic is to take conventional materials with interesting electronic order and attempt to gate them. This approach faces the fundamental difficulty that the field effect is essentially a surface phenomenon, requiring extremely thin samples where surface defects such as dangling bonds or chemical reactions with the environment can undermine bulk material properties (See, Novoselov, K. S. et al., *Proc. Natl. Acad. Sci. U.S.A.* 102, 10451-10453 (2005).).
Graphene Graphene has been shown to effectively carry both Josephson and spin-polarized currents injected from the contacting electrodes. However, a finite coherence length limits the length of such junctions to approximately one micron, reducing the system to essentially one dimension.

SUMMARY OF THE INVENTION

An embodiment of a graphene device of the present invention includes a layered structure, first and second electrodes, and a dopant island. The layered structure includes a conductive layer, an insulating layer, and a graphene layer. The insulating layer couples the conductive layer to the graphene layer. The first and second electrodes are electrically coupled to the graphene layer. In an embodiment, the dopant island is coupled to an exposed surface of the graphene layer between the first and second electrodes.

An embodiment of a method of using a graphene device of the present invention includes providing the graphene device. A voltage is applied to the conductive layer of the graphene device.

Another embodiment of a method of using a graphene device of the present invention includes providing the graphene device without the dopant island. A dopant island is placed on an exposed surface of the graphene layer between the first and second electrodes. A voltage is applied to the conductive layer of the graphene device. A response of the dopant island to the voltage is observed.

BRIEF DESCRIPTION OF THE DRAWINGS

The present invention is described with respect to particular exemplary embodiments thereof and reference is accordingly made to the drawings in which.

DETAILED DESCRIPTION OF THE INVENTION

Figure 1:
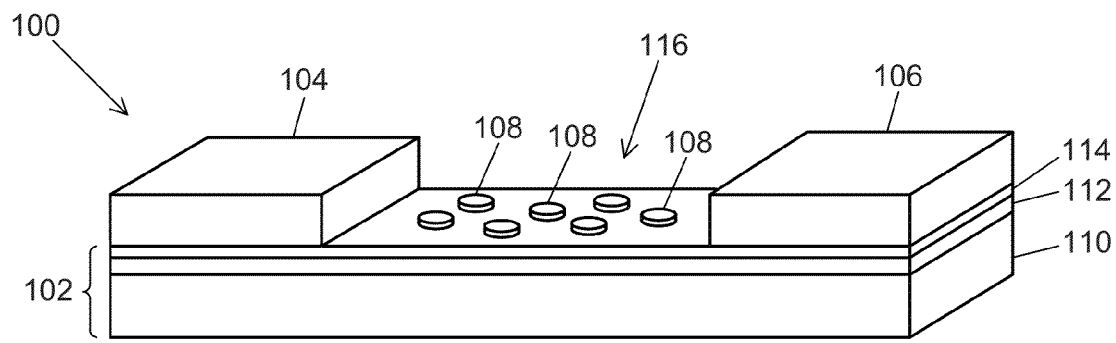
FIG. 1 illustrates an embodiment of a graphene device of the present invention.

Embodiments of the present invention include a graphene device and a method of using a graphene device, An embodiment of a graphene device of the present invention is illustrated in FIG. 1. The graphene device 100 includes a layered substrate 102, first and second electrodes, 104 and 106, and a dopant island or dopant islands 108. Layered substrate 102 includes a conductive layer 110, an insulating layer 112, and a graphene layer 114. First and second electrodes 104 and 106 are electrically coupled to graphene layer 114 and are located to provide an exposed surface 116 of graphene layer 114. Dopant island or dopant islands 108 are coupled to the surface 116 of graphene layer 114. In an embodiment, conductive layer 110 is heavily doped silicon (e.g., $n^+$ or $p^+$ Si) and insulating layer 112 is silicon oxide (e.g., $SiO_2$). Graphene layer 114 may be single-layer graphene or few-layer graphene (e.g., two or three layer graphene). In an embodiment, first and second electrodes 104 and 106 comprise a thin layer of Pd deposited onto graphene layer 114 (i.e., an adhesion layer) and an Au layer deposited onto the Pd layer.

Dopant island or islands 108 may be selected from the group of a superconducting material, a ferromagnetic material, an antiferromagnetic material, a photovoltaic material, a plasmonic material, a spintronic material, an organic material, or a biological material. According to an embodiment, a single dopant island 108 resides between first and second electrodes 104 and 106. According to another embodiment, a plurality of dopant islands 108 resides between first and second electrodes 104 and 106. In an embodiment, dopant islands 108 are a superconducting material (e.g., Sn islands).

In an embodiment, an average separation distance between dopant islands 108 is less than an average island dimension parallel to graphene layer 114. In another embodiment, the average separation distance between dopant islands 108 is less than three-quarters the average island dimension parallel to graphene layer 114. In yet another embodiment, the average separation distance between dopant islands 108 is less than one-half the average island dimension parallel to graphene layer 114. In an embodiment, a majority of dopant islands 108 have a minimum dimension parallel to graphene layer 114 of at least 2 nm. In another embodiment, the majority of dopant islands 108 have a minimum dimension parallel to graphene layer 114 of at least 5 nm. In yet another embodiment, the majority of dopant islands 108 have a minimum dimension parallel to graphene layer 114 of at least 10 nm. In an embodiment, a majority of dopant islands 108 are separated from others of dopant islands 108 by at least 1 nm. In another embodiment, a majority of dopant islands 108 are separated from others of dopant islands 108 by at least 2 nm. In yet another embodiment, the majority of dopant islands 108 are separated from others of dopant islands 108 by at least 5 nm.

Field-Effect Transistor (FET)

It will be readily apparent to one skilled in the art that layered substrate 102 and first and second electrodes 104 and 106 of graphene device 100 form a field-effect type structure similar to a field-effect transistor (FET). In other words, conductive layer 110 forms a gate and first and second electrodes 104 and 106 form a source and drain, respectively. Numerous modifications of the FET type structure of graphene device 100 may be made within the scope of the present invention. For example, graphene layer 114 might lie only between electrodes 104 and 106, or it might extend only partially under electrodes 104 and 106.

In another example, conductive layer 110 may be a thin conductive layer rather than a conductive substrate. According to this example, the thin conductive layer may lie between insulating layer 112 and a backing substrate or electrodes 104 and 106 might be coupled to a rigid structure leaving the thin conductive layer, insulating layer 112, and graphene layer 114 at least partially suspended between the first and second electrodes 104 and 106.

Fabrication

Fabricating graphene device 100 may begin with a high conductivity Si substrate, which becomes conductive layer 110. $SiO_2$ may be grown on a surface of the Si substrate, which becomes insulating layer 112.

Graphene (i.e., single- or few-layer graphene) may be exfoliated from graphite and placed on the $SiO_2$ surface, which becomes graphene layer 114. Alternatively, single- or few-layer graphene (or graphite) may be produced using chemical vapor deposition (CVD) (see Li, X. et. al., *Science* 324, 1312 (2009)). Graphene produced by CVD can be efficiently transferred to other substrates. Graphene layer 114 may be patterned using photolithography and etching. First and second electrodes 104 and 106 may be deposited onto graphene layer 114 by using, for example, a physical vapor deposition technique in conjunction with a mask.

Dopant island or islands 108 may be placed on graphene layer 114 in any of a number of ways. For example, some materials such as Sn will self assemble as islands if a thin layer of such a material is deposited onto graphene layer 114 at an appropriate temperature. Another example is to deposit material onto graphene layer 114 and then pattern it into dopant island or islands 108 by using photolithography and etching. Yet another example, which is more appropriate in a lab environment, is to physically place dopant island or islands 108 onto graphene layer 114 using a microscope (e.g., a scanning electron microscope). Other examples include chemical functionalization and wet assembly.

Structure

Figure 2:
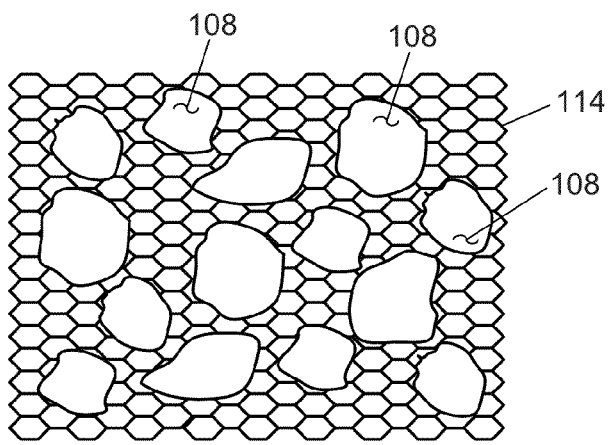
FIG. 2 illustrates a graphene layer and dopant islands in accordance with an embodiment of the present invention.

FIG. 2 illustrates an embodiment of graphene layer 114 and dopant islands 108 of the present invention. In this embodiment, graphene layer 114 exhibits a planar hexagonal structure. Also in this embodiment, dopant islands 108 exhibit irregular shapes.

Figure 3:
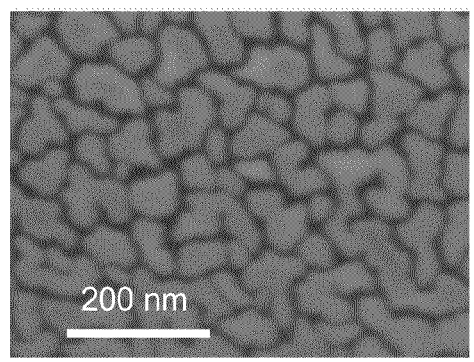
FIG. 3 is a scanning electron micrograph of Sn dopant islands on a graphene layer in accordance with an example of the present invention.

FIG. 3 is a scanning electron micrograph that provides an example of graphene layer 114 and dopant islands 108 of the present invention. Dopant islands 108 are Sn islands and appear as the lighter shaded features. Graphene layer 114 can be seen in the gaps between the Sn island. It appears in black.

Using a Graphene Device

An embodiment of a method of using a graphene device includes providing graphene device 100. The method further includes applying a voltage to the conductive layer 110. In an embodiment, dopant island or islands 108 include a superconducting material. According to this embodiment, graphene device 100 may be used as a superconducting FET, a photon detector, a particle detector, a magnetometer, a superconducting mechanical device, or for some other suitable application. In another embodiment, dopant island or islands 108 include a chemically sensitive material. According to this embodiment, graphene device 100 may be used as a chemical sensor or for some other suitable purpose.

Another embodiment of a method of using a graphene device of the present invention includes providing a graphene device 200. The method further includes placing a dopant island or islands on an exposed surface of graphene layer 114. Placement of the dopant island or islands may take place within a controlled environment (e.g., under vacuum or at low temperature). The method further includes applying a voltage to conductive layer 110 and observing a response of the dopant island or islands to the applied voltage. The dopant island or islands may be selected from the group of a superconducting material, a ferromagnetic material, an antiferromagnetic material, a photovoltaic material, a plasmonic material, a spintronic material, an organic material, a biological material, or some other material or substance for which a response to an applied voltage is to be observed. In an embodiment, the response of the dopant island or islands is observed using a microscope. For example, the microscope may be an electron microscope (e.g., a scanning or transmission electron microscope) or a scanning probe microscope (e.g., an atomic force microscope). Graphene device 200 may become a commercially available consumable for microscopy or other types of scientific or technical observation.

Other Embodiments

Figure 4:
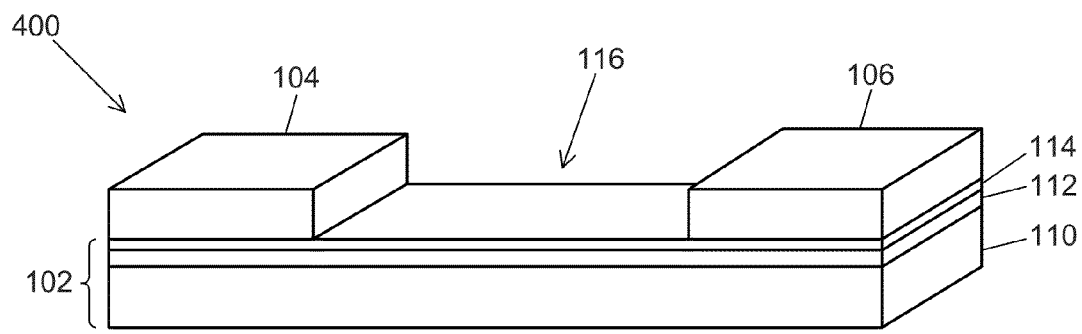
FIG. 4 illustrates a graphene device in accordance with an embodiment of the present invention.

A graphene device in accordance with an embodiment of the present invention is illustrated in FIG. 4. The graphene device 400 is graphene device 100 without the dopant island or islands 108.

Figure 9:
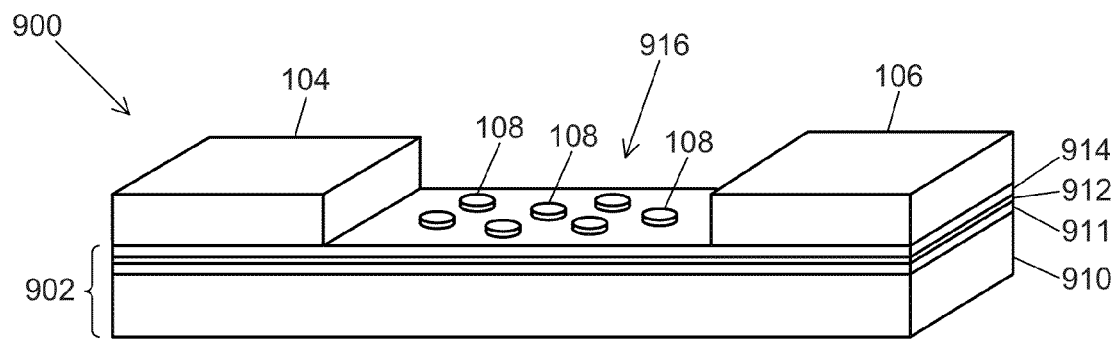
FIG. 9 illustrates an embodiment of a graphene device of the present invention.

Another embodiment of a graphene device of the present invention is illustrated in FIG. 9. The graphene device 900 includes a layered substrate 902, first and second electrodes, 104 and 106, and a dopant island or islands 108. The layered substrate includes a base material 910, a conductive layer 911, an insulating layer 912, and graphene layer 914. First and second electrodes 104 and 106 are electrically coupled to the graphene layer 914 and are located to provide an exposed surface 916 of the graphene layer 914. Dopant island or islands 108 are coupled to exposed surface 916 of the graphene layer 914. Base material 910 may be an insulator, a semiconductor, or a metal. Conductive layer 911 may be a metal, graphite, single-layer graphene, or few-layer graphene. For example, conductive layer 911 and graphene layer 914 may be single- or few-layer graphene that are separated by insulating layer 912, which may be produced between the graphene layers by intercalating atoms or molecules that form the insulating layer 912.

Examples

The easily accessible two-dimensional electron gas (2DEG) in graphene sheets (see, Geim, A. K., et al., *Nat. Mater.* 6, 183-191 (2007)) provides an ideal platform on which to tune, via application of an electrostatic gate, the coupling between any type of electronically ordered dopants deposited on its surface. To demonstrate this concept, a self-assembly method to induce a tunable superconducting transition was employed. (The transition is quantitatively described by Berezinskii-Kosterlitz-Thouless (BKT) vortex unbinding in two-dimensions.) Strong screening of the vortex-antivortex interaction resulted in an exceptionally sensitive response to applied magnetic fields. The self-assembly method and tunable coupling could be extended to other electronic order parameters such as ferro/antiferromagnetism, charge/spin density waves, etc.

Limitations of using the field effect to produce electronic devices can be avoided by utilizing a two-dimensional material, atomically thin sheets of graphene. The bipolar 2DEG present in graphene is markedly different from the buried 2DEGs found at oxide interfaces or in GaAs heterostructures in that it is "open" to the environment with a stable and inert surface. Species deposited onto the surface, such as metal clusters, can then efficiently act as dopants by coupling their electronic order directly into the electron gas. The low density of electrons in this 2DEG, relative to bulk values, and weak intrinsic interactions such as spin-orbit coupling, limit back-action of the electron gas on dopant properties. Exposed graphene provides a near-ideal open platform for the general study and exploitation of tunable 2D phase transitions.

Fully-Tunable 2D Superconductivity

Figure 5:
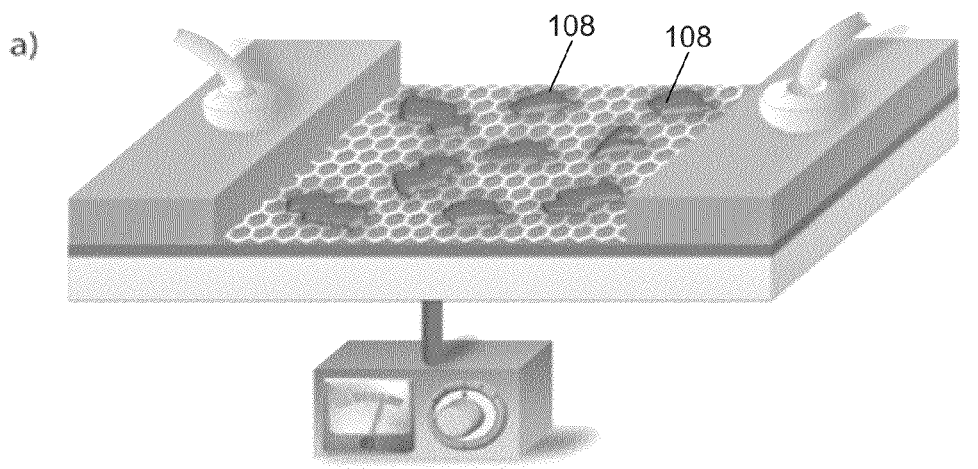
FIG. 5a is a schematic of device configuration and measurement setup in accordance with the present invention.
FIG. 5b is a scanning electron micrograph of Sn island morphology on the graphene sheet in accordance with the present invention.
FIG. 5c is a graph of four terminal sheet resistance as a function of gate voltage for a device in accordance with the present invention.
Figure 5:
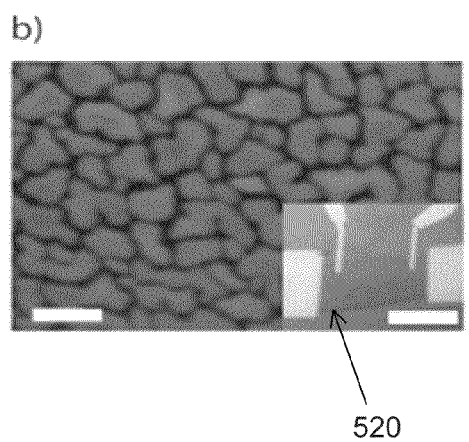
Figure 5:
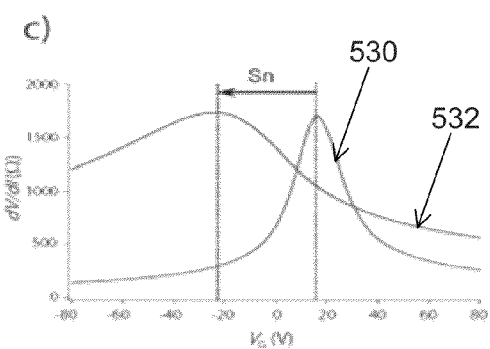

As a demonstration of this approach, fully-tunable 2D superconductivity was considered. In order to maintain coherence over longer distances while retaining the unique properties of the graphene sheet, the present invention employs a geometry, as depicted in FIG. 5a, where a large array of dopant islands is placed in a non-percolating network on top of the graphene sheet (See, Feigel'man et al., *Jetp Lett.* 88, 862-866 (2008); and Lutchyn et al., *Phys. Rev. Lett.* 101 (2008).). FIGS. 5a, 5b, and 5c show an overview of grapheme device 100 and its basic properties. Dopant islands 108 correspond to a dopant with desired electronic order. The electronic coupling between dopant islands 108 can be tuned by varying the electrostatic gate voltage applied to a back gate represented by the tuning knob. The outer contacting electrodes made of non superconducting Pd/Au pads are used to probe the electronic transport through the sheet.

The present invention avoids complicated lithographic patterning and exploits the poor wettability of graphite to produce an array of submicron islands. Low melting point metals, such as the elemental superconductor Sn, readily form self-assembled islands when deposited on pristine graphene at room temperature, as depicted in FIG. 5b. Typically, 10 nm of nominal deposition thickness results in islands with 80±5 nm diameter and 25±10 nm gaps between them. In general, many different materials with different electronic order parameters can be deposited via this process by controlling the graphene substrate temperature during deposition, and other deposition methods, including chemical functionalization and wet self-assembly can be used as well. The scale bar in FIG. 5b is 100 nm. The inset 520 in FIG. 5b provides an optical image of a typical device showing the four probe configuration, where the scale bar in the inset is 10 microns.

FIG. 5c provides four terminal sheet resistance as a function of gate voltage for a device before, shown in plot 530, and after, shown in plot 532, Sn deposition. The dotted lines indicate the charge neutrality point before and after deposition where the average charge density vanishes. The arrow indicates the shift in this point after deposition of Sn.

FIG. 5c displays the evolution of the room-temperature field-effect properties of a device as Sn is deposited via the present invention. Although 40% of the graphene surface is coated by Sn islands after the deposition, many of the original electronic properties of graphene remain intact, including bipolar transport and carrier mobilities >1000 $cm^2/(V \cdot s)$. The three main effects of the Sn deposition are a shift in the charge neutrality point (Dirac point) to more negative voltages, a modest decrease in mobility, and a pronounced asymmetry between electron and hole transport.

All three of these effects are well described by inhomogeneous doping due to charge transfer from the metal islands to the graphene sheet. From the shift in the charge neutrality point and the coverage level, it is inferred that the Sn transfers $9 \pm 2 \times 10^{12}$ $cm^{-2}$ electrons to the graphene, as expected (See, Giovannetti, G. et al., *Phys. Rev. Lett.* 101 (2008).) from the difference in work functions between the two materials ($\Phi_G$=4.5 eV, $\Phi_{Sn}$=4.42 eV) and in agreement with recent experiments using other metals (See, Lee, E. J. H., et al., *Nat. Nanotechnol.* 3, 486-490 (2008).). This induced charge reduces the mobility of both types of carriers via charged impurity scattering (See, Chen, J. H. et al., *Nat. Phys.* 4, 377-381 (2008).) while the asymmetry in transport occurs because the holes experience the pinned Fermi level under the Sn islands as a potential barrier, while electrons experience a potential well.

Figure 6:
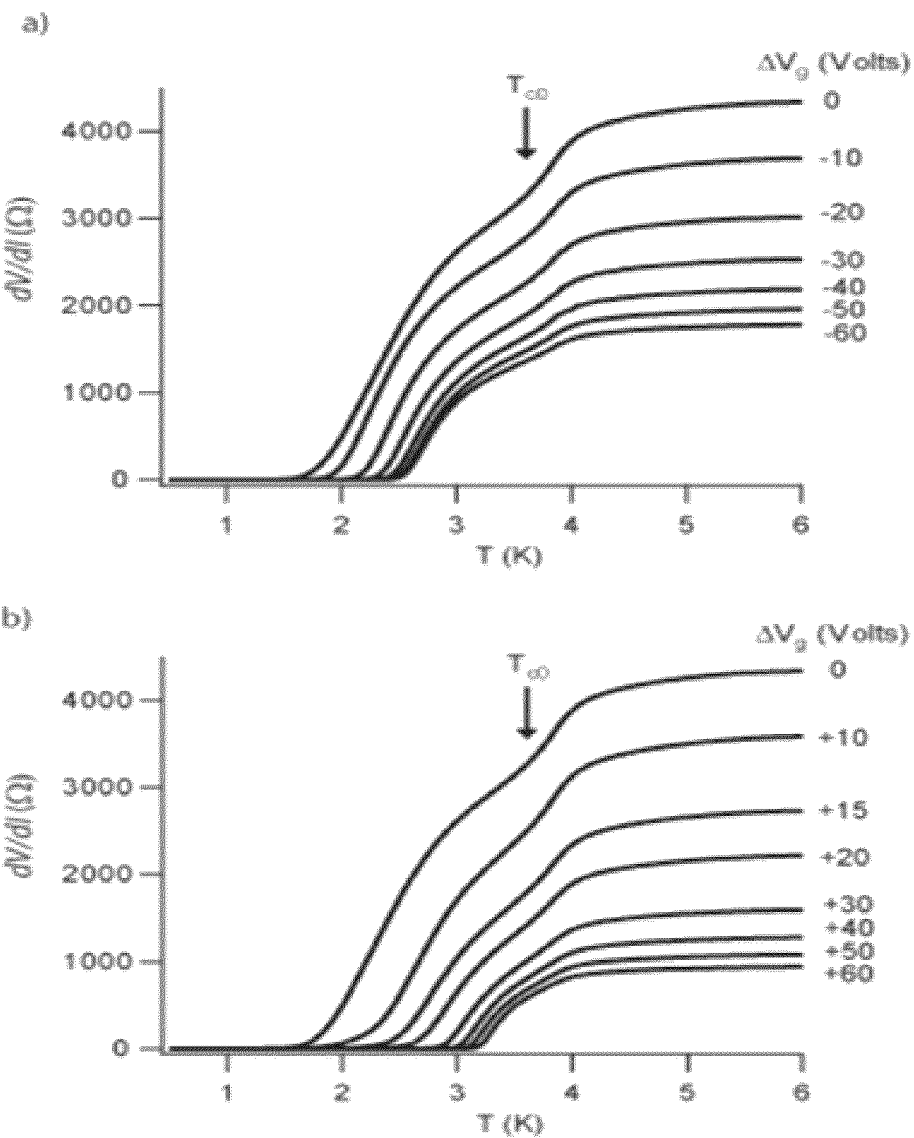
FIG. 6a is a plot in accordance with the present invention.
FIG. 6b is a plot in accordance with the present invention.

More interesting than the influence of the Sn islands on the normal state properties of graphene is the effect the superconducting correlations will have on transport through the graphene via the proximity effect. FIG. 6 shows the sheet resistance versus temperature for a variety of gate voltages on both the hole, as shown in FIG. 6a, and electron, as shown in FIG. 6b, sides of the charge neutrality point. Each curve exhibits two distinct features, a high temperature partial drop in resistance that occurs at ~3.5 K (independent of gate voltage), and a broad transition between 3 K and 1 K to a state of zero resistance that is strongly dependent on the applied gate voltage. FIGS. 6a, and 6b show transition to the 2D superconducting state. Sheet resistance versus temperature for various gate voltages, $\Delta V_g$, referenced to the charge neutrality point. In FIG. 6a, $\Delta V_g < 0$ corresponds to hole transport, whereas, $\Delta V_g > 0$ in FIG. 6b corresponds to electron transport through the graphene sheet. The arrow labeled $T_{c0}$ indicates the first partial resistance drop corresponding to the superconducting transition of the Sn islands.

The first partial resistance drop, as indicated by the arrows in FIGS. 6a and 6b, is due to Cooper pairs condensing in the Sn islands. By fitting the fluctuation enhanced conductivity above the transition, a mean-field transition temperature ($T_{c0}$) for the Sn islands of 3.54±0.02 K independent of gate voltage was extracted. Due to the weak Coulomb repulsion in graphene, superconducting correlations were expected to extend efficiently within the graphene sheet. However, even below $T_{c0}$, thermally induced vortices destroy global phase coherence and produce dissipation due to a finite flux flow resistance. At still lower temperatures, vortices with opposite circulation form bound pairs allowing a supercurrent to flow.

Figure 7:
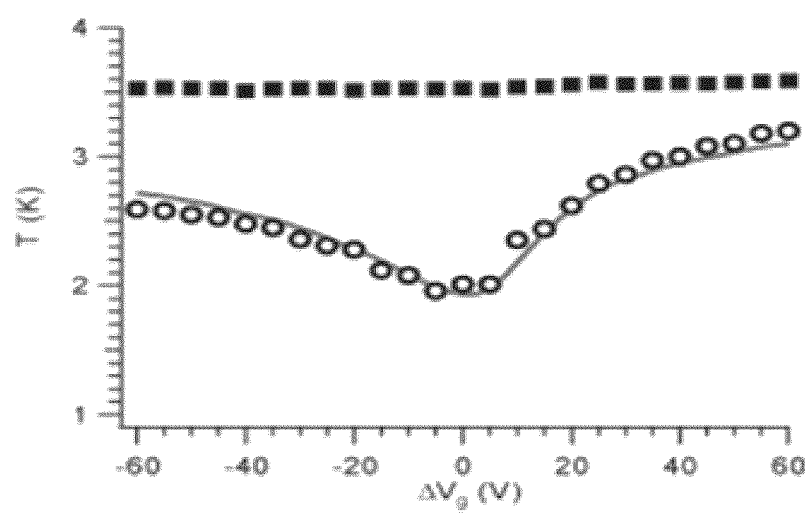
FIG. 7 is a plot in accordance with the present invention.

Analysis of the transition to the fully superconducting state shows that it follows the universal form $R_\square(T) \sim \exp[-b(T-T_{BKT})^{-1/2}]$ characteristic of the BKT vortex-unbinding transition in two dimensions, where b is a constant of order unity governing the vortex-antivortex interaction strength and $T_{BKT}$ is the vortex unbinding temperature. FIG. 7 shows the resulting $T_{BKT}$ (open circles) extracted from fitting the resistance curves at different gate voltages.

From the mean free path extracted from field effect measurements at 6 K and the coherence length of Sn, it is inferred that the material produced by the present invention is in the dirty limit, ($l_{mfp} < \xi_0$). A dirty 2D superconductor will undergo a BKT transition at a temperature given by $$\frac{T_{c0}}{T_{BKT}}\left\{\frac{\Delta(T_{BKT})}{\Delta(0)}\tanh\left[\frac{\Delta(T_{BKT})}{2k_B T_{BKT}}\right]\right\} = \frac{\varepsilon_c R_N}{R_0} \quad (1)$$

where, $\Delta(T)$ is the superconducting energy gap, $R_N$ is the normal state sheet resistance, $$R_0 \equiv \frac{2.18\hbar}{e^2} \cong 8.96 \text{ k}\Omega$$

and $\varepsilon_c$ is an effective dielectric constant that describes the material dependent screening of the attractive vortex-antivortex interaction. Using the weak-coupling BCS limit for the superconducting gap and the sheet resistance measured at 6 K, the $T_{BKT}$ extracted above is fitted and find $\varepsilon_c=2.40\pm0.05$ (solid curve in FIG. 7), which is twice the value seen in quench condensed Hg—Xe films. This implies that the vortices and antivortices are relatively weakly bound in our system. FIG. 7 shows an analysis of gate voltage dependence of the superconducting transition. The mean field transition temperature, $T_{c0}$ (black squares), and vortex-unbinding temperature, $T_{BKT}$ (open circles) as a function of gate voltage as extracted from the resistance versus temperature curves presented in FIG. 6. The solid line is a fit of $T_{BKT}$ using equation (1) and the measured normal state properties of the device.

Figure 8:
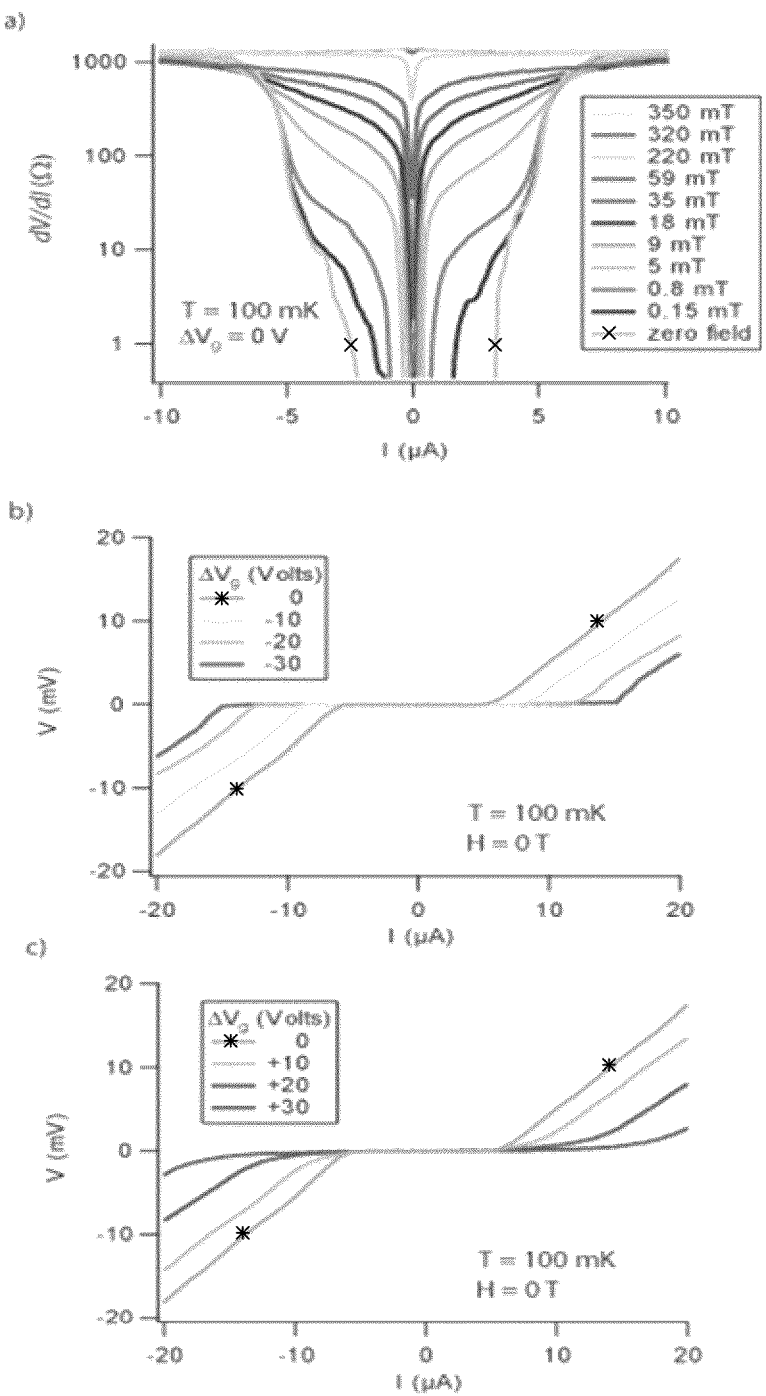
FIG. 8a is a plot in accordance with the present invention.
FIG. 8b is a plot in accordance with the present invention.
FIG. 8c is a plot in accordance with the present invention.

In addition to tuning the transition temperature of the material, the electrostatic gate allows for the tuning of the ground state properties of the system as well. The large value of $\varepsilon_c$ implies that the effects of induced vortices will be enhanced due to screening of the vortex-antivortex binding interaction. Using an applied magnetic field perpendicular to the sheet to induce vortices, it is found that the critical current is extremely sensitive to magnetic perturbations, as shown in FIG. 8a. At the lowest fields, it is estimated to have a sensitivity of 3.5 μA/mT. FIGS. 8a, 8b, and 8c show ground state transport properties measured at 100 mK. FIG. 8a provides differential conductance as a function of bias current with the gate voltage held at the charge neutrality point, $\Delta V_g=0$, for several magnetic fields applied perpendicular to the sheet to induce vortices. Current-voltage curves taken at zero magnetic field, corresponding to FIG. 8b hole transport and to FIG. 8c electron transport in the graphene sheet for gate voltages, $\Delta V_g$, referenced to the charge neutrality point.

Another useful probe of the induced 2D superconducting ground state is the current-voltage characteristics at different applied gate voltages as shown in FIGS. 8b and 8c. The gate tunable critical current is qualitatively similar to isolated graphene Josephson junctions with the exception that, in our devices, critical current densities ($I_c$/width) comparable to submicron graphene Josephson junctions are maintained over distances of tens of microns, demonstrating the fully two-dimensional phase coherence in this system.

The present invention provides a method to induce two-dimensional superconducting order on a graphene sheet and tune all of its material properties: transition temperature, critical field, and critical current via an electrostatic gate. Arranging the islands into regular arrays or superlattices could lead to interesting frustration effects as a function of applied magnetic and electric fields. While the properties of this system using electron transport has been probed, the easily accessible interface allows application of a myriad of chemical modifications and local characterization techniques such as optical excitation, scanning probe microscopy, photoemission, etc. The ease of fabrication and considerable versatility of deposition materials make this an attractive platform for investigating diverse electronic orders and designing functional materials.

Materials and Methods

Kish graphite was exfoliated using the scotch tape method[1] onto degenerately doped (p<0.005 mOhms-cm) silicon wafers coated with 285 nm of thermal oxide (115 aF/um²). Single-layer graphene flakes were identified by contrast measurements using optical microscopy connected to a CCD camera and confirmed via analysis with a micro-Raman spectrometer. In order to produce the island network, Sn (99.999% purity) was evaporated using an electron gun in high vacuum (ca 10-7 torr) onto graphene substrates in an amount equivalent to a 10 nm thickness for a fully covered layer. Scanning electron micrographs and atomic force microscopy scans were analyzed using standard particle counting analysis software (ImageJ) to determine film morphology. Four-probe contacts were defined via electron beam lithography and a Pd/Au 10/50 nm bilayer was evaporated as metal electrodes. The samples were thermally anchored to the cold stage of He-3 and Dilution cryostats and connected to highly RF filtered lines. Linear response and differential conductance were measured with standard low frequency lock-in techniques using low excitation currents in the range 10-100 nA. More than 5 samples were tested and showed similar results.

CONCLUSION

As used herein and in the appended claims, the singular forms "a", "and", and "the" include plural referents unless the context clearly dictates otherwise.

The foregoing detailed description of the present invention is provided for the purposes of illustration and is not intended to be exhaustive or to limit the invention to the embodiments disclosed. Accordingly, the scope of the present invention is defined by the appended claims.

REFERENCES

1. Ahn, C. H., et al., Electrostatic modification of novel materials. *Rev. Mod. Phys.* 78, 1185-1212 (2006).
2. Ahn, C. H., Triscone, J. M. & Mannhart, J. Electric field effect in correlated oxide systems. *Nature* 424, 1015-1018 (2003).
3. Hwang, H. Y. Atomic control of the electron structure at complex oxide heterointerfaces. *MRS Bull.* 31, 28-35 (2006).
4. Takahashi, K. S., et al., Local switching of two-dimensional superconductivity using the ferroelectric field effect. *Nature* 441, 195-198 (2006).
5. Ueno, K., et al., Electric-field-induced superconductivity in an insulator. *Nat. Mater.* 7, 855-858 (2008).
6. Caviglia, A. D., et al., Electric field control of the LaAlO3/SrTiO3 interface ground state. *Nature* 456, 624-627 (2008).
7. Siemons, W., et al., Origin of charge density at LaAlO3 on SrTiO3 heterointerfaces: Possibility of intrinsic doping. *Phys. Rev. Lett.* 98, 4 (2007).
8. Novoselov, K. S., et al., Two-dimensional atomic crystals. *Proc. Natl. Acad. Sci. U.S.A.* 102, 10451-10453 (2005).
9. Li, X. et. al., Large-area synthesis of high-quality and uniform graphene films on copper foils, *Science* 324, 1312 (2009).
10. Geim, A. K. & Novoselov, K. S. The rise of graphene. *Nat. Mater.* 6, 183-191 (2007).
11. Feigel'man, M. V. et al., Proximity-induced superconductivity in graphene. *Jetp Lett.* 88, 862-866 (2008).
12. Lutchyn, R. M. et al., Dissipation-driven quantum phase transition in superconductor-graphene systems. *Phys. Rev. Lett.* 101 (2008)).
13. Giovannetti, G., et al., Doping graphene with metal contacts. *Phys. Rev. Lett.* 101 (2008).
14. Lee, E. J. H., Balasubramanian, K., Weitz, R. T., Burghard, M. & Kern, K. Contact and edge effects in graphene devices. *Nat. Nanotechnol.* 3, 486-490 (2008).
15. Chen, J. H., et al., Charged-impurity scattering in graphene. *Nat. Phys.* 4, 377-381 (2008).

What is claimed is:

1. A graphene device comprising:
    a base material;
    a graphene layer disposed on the base material, the graphene layer being a planar graphene layer including a first side and a second side, the first side of the graphene layer being disposed on the base material, and the first side and the second side of the graphene layer being insulated from one another by intercalated atoms or molecules;
    a first electrode disposed on the second side of the graphene layer;
    a second electrode disposed on the second side of the graphene layer; and
    a first dopant island disposed on the second side of the graphene layer between the first and the second electrodes.

2. The graphene device of claim 1 wherein the second side of the graphene layer comprises a single-layer of graphene.

3. The graphene device of claim 1 wherein the second side of the graphene layer comprises a few layers of graphene.

4. The graphene device of claim 1 wherein the first dopant island is selected from the group consisting of a superconducting material, a ferromagnetic material, an antiferromagnetic material, a photovoltaic material, a plasmonic material, a spintronic material, an organic material, and a biological material.

5. The graphene device of claim 1 further comprising:
    a plurality of dopant islands disposed on the second side of the graphene layer between the first and the second electrodes, the first dopant island being one of the plurality of dopant islands.

6. The graphene device of claim 5 wherein the plurality of dopant islands comprise a superconducting material.

7. The graphene device of claim 5 wherein an average separation distance between dopant islands of the plurality of dopant islands is less than an average dopant island dimension parallel to the graphene layer.

8. The graphene device of claim 7 wherein the average separation distance between the dopant islands is less than three-quarters the average dopant island dimension parallel to the graphene layer.

9. The graphene device of claim 7 wherein the average separation distance between the dopant islands is less than one-half the average dopant island dimension parallel to the graphene layer.

10. The graphene device of claim 5 wherein dopant islands of the plurality of dopant islands have a dimension parallel to the graphene layer of at least 2 nanometers.

11. The graphene device of claim 10 wherein the dopant islands have a dimension parallel to the graphene layer of at least 5 nanometers.

12. The graphene device of claim 10 wherein the dopant islands have a dimension parallel to the graphene layer of at least 10 nanometers.

13. The graphene device of claim 5 wherein dopant islands of the plurality of dopant islands are separated from others of the dopant islands by at least 1 nanometer.

14. The graphene device of claim 13 wherein the dopant islands are separated from others of the dopant islands by at least 2 nanometers.

15. The graphene device of claim 13 wherein the dopant islands are separated from others of the dopant islands by at least 5 nanometers.

16. The graphene device of claim 1 wherein the base material comprises an insulator.

17. A method of using a graphene device comprising:
    providing the graphene device comprising:
        a base material;
        a graphene layer disposed on the base material, the graphene layer being a planar graphene layer including a first side and a second side, the first side of the graphene layer being disposed on the base material, and the first side and the second side of the graphene layer being insulated from one another by intercalated atoms or molecules;
        a first electrode disposed on the second side of the graphene layer;
        a second electrode disposed on the second side of the graphene layer; and
        a first dopant island disposed on the second side of the graphene layer between the first and the second electrodes; and
    applying a voltage to the first side of the graphene layer.

18. The method of claim 17 wherein the first dopant island is selected from the group consisting of a superconducting material, a ferromagnetic material, an antiferromagnetic material, a photovoltaic material, a plasmonic material, a spintronic material, an organic material, and a biological material.

19. The method of claim 17 wherein the first dopant island comprises a superconducting material.

20. The method of claim 19 further comprising:
operating the graphene device as a device selected from the group consisting of a superconducting field effect transistor, a superconducting photon detector, a particle detector, a magnetometer, and a superconducting mechanical device.

21. The method of claim 17 wherein the first dopant island comprises a chemically sensitive material.

22. The method of claim 21 further comprising:
operating the graphene device as a chemical detector.

23. The method of claim 17 further comprising:
observing a response of the first dopant island to the voltage.

24. The method of claim 23 wherein the first dopant island is selected from the group consisting of a superconducting material, a ferromagnetic material, an antiferromagnetic material, a photovoltaic material, a plasmonic material, a spintronic material, an organic material, and a biological material.

25. The method of claim 23 wherein the observing comprises observing the response in a microscope.

26. The method of claim 25 wherein the microscope comprises an electron microscope.

27. The method of claim 25 wherein the microscope comprises a scanning probe microscope.

28. The method of claim 17 wherein the base material comprises an insulator.

\* \* \* \* \*